United States Patent [19]

Garner et al.

[11] 4,022,802

[45] May 10, 1977

[54] PROCESS FOR THE MANUFACTURE OF N-SUBSTITUTED INDOLES

[75] Inventors: Robert Garner, Ramsbottom Bury, England; Max Dünnenberger, Frenkendorf, Switzerland

[73] Assignee: Ciba-Geigy AG, Basel, Switzerland

[22] Filed: May 12, 1975

[21] Appl. No.: 576,751

Related U.S. Application Data

[63] Continuation-in-part of Ser. No. 306,754, Nov. 15, 1972, abandoned.

[30] Foreign Application Priority Data

Nov. 26, 1971  Switzerland ................... 17240/71

[52] U.S. Cl. .......................................... 260/319.1
[51] Int. Cl.² .............. C07D 209/04; C07D 209/10
[58] Field of Search ............................... 260/319.1

[56] References Cited

UNITED STATES PATENTS 3,478,208  11/1969  Horrocks et al. ............... 260/319.1

OTHER PUBLICATIONS

Hobbs et al., "J.A.C.S.", vol. 84, pp. 45 and 49 (1962).

*Primary Examiner*—Ethel G. Love
*Attorney, Agent, or Firm*—Edward McC. Roberts; Michael W. Glynn; Prabodh I. Almaula

[57] ABSTRACT

A process for the manufacture of N-substituted indoles, wherein an indole is treated with a base in dimethyl sulphoxide, or in a dipolar aprotic solvent with a tertiary acid amide group, such as dimethyl formamide, and subsequently reacted with an alkylating or aralkylating agent and the new indoles carrying in the 1-position an alkyl radical with at least 6 carbon atoms or an alkenyl radical with at least 3 carbon atoms, or an alkyl or alkenyl radical which is substituted with halogen, a hydroxy, cyano, carboxy, lower alkoxy, alkylamino or alkoxycarbonyl group.

6 Claims, No Drawings

PROCESS FOR THE MANUFACTURE OF N-SUBSTITUTED INDOLES

This is a continuation-in-part of our patent application Ser. No. 306,754, filed Nov. 15, 1972, now abandoned The present invention provides a new process for the manufacture of N-substituted indoles in dimethyl sulphoxide or in a dipolar aprotic solvent with a tertiary acid amide group, such as dimethyl formamide or dimethyl acetamide, and by means of which it is possible to manufacture a number of new and known indoles in good yields.

From British Pat. No. 1,124,594 it is known to alkylate N-heterocycles in dimethyl sulphoxide. According to the process described therein, N-heterocycles, in particular carbazoles, phenothiazines and acridones, are treated with alkylating agents at temperatures above 50° C, preferably at 80° to 100° C. An acid binding agent, in particular 50% aqueous sodium hyroxide solution, is added in the course of the reaction.

In addition, it is known from the literature (C.F. Hobbs et al., J. Amer. Chem. Soc. 1961, 84, 43) to alkylate pyrrole by firstly converting it into the alkali salt in tetrahydrofuran with potassiumm or sodium hydride, dissolving this salt in dimethyl sulphoxide and adding the alkylating agent to this solution. The reaction temperature is given as 65° C.

In an attempt to alkylate indoles according to the directions given in British Pat. No. 1,124,594, it was observed that side reactions occur, for which reason the yields were always less than 60% of the theory.

The method of C.F. Hobbs has the disadvantage that dangerous substances, such as potassium or sodium hydride and the easily inflammable tetrahydrofuran, are necessary. Moreover, the process is complicated because two solvents are used.

It has now been found that in dimethyl sulphoxide, or in a dipolar aprotic solvent with a tertiary acid amide group, such as dimethyl formamide or dimethyl acetamide, it is possible to substitute indoles in a simple manner and with good yields if, before the addition of the alkylating agent, the N-alkali salt is manufactured from the indole with the aid of bases, e.g. alkali hydroxides, and subsequently the alkylating agent is added in such a way that the temperature on no account rises above 50° C.

It is important that as little water as possible is present in the reaction mixture. The bases are therefore added in non-aqueous solution or preferably in solid form.

Commercial bases in solid form can be used. Thus, the use of solid commercial KOH is contemplated for use in the present invention as illustrated in Example 1. Commercial KOH is known to contain about 83–86 percent KOH, the remainder consisting of water (10–13 percent) and $K_2CO_3$ (2–3 percent) as evidenced by Merck Index, 7th Edition, page 842. Such small amounts of water have not been found to adversely affect the reaction, since, with reference to the reaction mixture in toto, less than 2% is water. Thus, water can be said to be substantially absent from the reaction mixture. Similar remarks are valid for NaOH in Example 2.

It is expedient to manufacture the N-alkali salt directly in the dimethyl formamide or dimethyl sulphoxide solution in which the alkylation or aralkylation will be subsequently carried out. As bases there are used alkali hydroxides, such as sodium hydroxide, potassium hydroxide or lithium hydroxide, or organic bases, such as tetramethylammonium hydroxide. In this way it is possible to avoid side reactions (such, for instance, as the hydrolysis of the alkyl halides used as alkylating agent) which occur on so inconveniently large a scale when the directions of the cited British patent are followed. The process is simple and not dangerous.

The invention therefore relates to a process for the manufacture of N-substituted indoles, wherein an indole is treated with a base in dimethyl sulphoxide, or in a dipolar aprotic solvent with a tertiary acid amide group, such as dimethyl formamide or dimethyl acetamide, and subsequently reacted with a compound of the formula $$R - X,$$

wherein X represents a leaving group, in particular a halogen atom, a sulphate or sulphonate group, and R represents an aralkyl, alkyl or alkylene radical which is optionally substituted by, for example, carboxylic acid, carboxylic acid ester, alkoxy or alkylamino groups, with an alkene, whose double bond is substituted with an electrophilic substituent, in particular a cyano or carbalkoxy group, or with an epoxide.

The temperature is advantageously between room temperature and 50° C. To keep the reaction time brief, it can be of advantage to use an excess of alkylating agent. This is preferably in a quantity of from 0 to 50%.

Possible compounds which can be substituted at the nitrogen by method according to the invention are chiefly indoles which are substituted with alkyl or alkoxy radicals containing preferably 1 to 4 carbon atoms, or with aryl radicals or halogen atoms. By aryl radicals are meant in particular radicals of the benzene series, such as phenyl, tolyl, chlorophenyl and methoxyphenyl radicals.

Examples of such indoles are:

2-methyl-indole,
2-ethyl-indole,
2-phenyl-indole,
2-tolyl-indole,
2,3-dimethyl-indole,
2-methyl-5-ethoxy-indole,
2-methyl-5-methoxy-indole.

As alkylating agents there are used above all benzyl halides or alkyl and alkenyl halides with up to 18 carbon atoms. These alkyl radicals may be substituted, for example with carboxyl, hydroxy, low molecular alkoxy, alkylamino or alkoxycarbonyl radicals. Also suitable are epoxides, such as ethylene oxide or, for example, ethylene oxides substituted by alkyl groups. Finally, mention may be made of compounds with double bonds polarised by electrophilic substituents, e.g. ethylene substituted with cyano, carboxy or lower carbalkoxy groups. The terms "lower" or "low molecular" indicate compounds with 1 to 4 carbon atoms.

As examples of alkylating agents there may be cited:

ethyl bromide
allyl chloride
benzyl chloride
n-propyl bromide
isopropyl bromide n-butyl bromide
n-pentyl bromide
n-hexyl bromide
n-heptyl bromide
n-octyl bromide
-n-nonyl bromide
n-decyl bromide
n-dodecyl bromide
stearyl bromide
chloroethyl acetate
bromethyl acetate
methylmethane sulphonate
p-ethyltoluene sulphonate
dimethyl sulphate
vinyl cyanide
methyl or ethyl acrylate
ethylene oxide
propylene oxide
3-chloropropylene oxide.

The compounds obtained according to the invention are valuable dyestuff intermediates. In particular, they are used for the manufacture of colour formers. These are obtained, for example, by condensing 2 moles of indole with one mole of the anhydride of an aromatic 1, 2-dicarboxylic acid. In this way products are obtained with which it is possible to manufacture pressure-sensitive recording paper by processes known in the art. A particular advantage is that the images produced with such colour formers can be copied with all conventional processes. The indoles manufactured according to the invention, if they carry in the 1-position alkyl or alkyl radicals which contain more than 5 carbon atoms or which are substituted with halogen, hydroxy, cyano, carboxy, lower alkoxy, alkylamino or alkoxycarbonylamino groups, have not yet been described in the literature and are therefore also claimed. The colour formers obtainable from these new indoles and an aromatic dicarboxylic acid anhydride are distinguished by particularly good solubility properties.

Examples of such compounds are:

1-allyl-2-methyl-indole,
1-isopropyl-2-methyl-indole,
1-n-propyl-2,3-dimethyl-indole,
1-n-butyl-2-methyl-indole,
1-isobutyl-2 -methyl-indole,
1-n-pentyl-2-methyl-indole,
1-n-hexyl-2-methyl-indole,
1-n-heptyl-2-methyl-indole,
1-n-octyl-2-methyl-indole,
1-n-decyl-2-methyl-indole,
1-stearyl-2-methyl-indole,
1-n-dodecyl-2-methyl-indole
1-(2'-carbethoxy)-ethyl-2-methyl-indole,
1-(2'-carbopropoxy)-ethyl-2-methyl-indole,
1-n-nonyl-2-methyl-indole
1-n-butyl-2-methyl-5-methoxy-indole,
1-n-octyl-2-methyl-indole,
1-($\beta$-cyanoethyl)-2-methyl-indole,
1-($\beta$-hydroxypropyl)-2-methyl-indole,
1-($\beta$-methoxycarbonylethyl)-2-methyl indole.

The following Example will serve to illustrate the invention, the parts and percentages being by weight unless otherwise stated.

131.2 parts of 2-methyl-indoles are dissolved at 45–50° C in 400 parts by volume of dimethyl sulphoxide. The solution is treated with 77 parts of solid potassium hydroxide (commercial grade). The mixture is stirred for about 10 minutes, then 134 parts of ethyl bromide are added within 1½ hours in such a manner that the temperature does not rise above 50° C. If necessary, the mixture is cooled.

Upon completion of the addition of ethyl bromide, the mixture is stirred for 3 hours at 50° C. The course of the reaction can be followed by a thin-layer chromatography. When all the 2-methyl-indole has been reacted, the mixture is cooled to about 25° C and the precipitated potassium bromide is separated by filtration. The potassium bromide is washed with about 25 parts by volume of dimethyl sulphoxide and the washings are combined with the filtrate, which is then fractionated under vacuum. About 350 to 400 parts by volume of dimethyl sulphoxide distill at a pressure of 18 mm Hg and initially at 85° C to 86° C. Then follows a fraction of a product which contains dimethyl sulphoxide as impurity and boils at 86° to 149° C, and finally 100 by 120 parts of 1-ethyl-2-methyl-indole (b.p. 149–151° C) are obtained (63% to 73% of theory).

The recovered dimethyl sulphoxide is used in the succeeding batches as solvent together with the fraction containing dimethyl sulphoxide as impurity. From the second and further batches are obtained in this way 140 to 150 parts respectively of pure 1-ethyl-2-methyl-indole (b.p. 126° C, $nD^{20}$ 1,5860), corresponding to 88% to 95% of theory. By using an equivalent amount of an alkyl bromide with at least 4 carbon atoms instead of ethyl bromide, the alkylated indole separates from the dimethyl sulphoxide and a two-phase reaction mixture is formed from which the layer consisting of the alkylated indole is isolated in a separating funnel. The crude product is washed with water. A further purification, e.g. by distillation, is not necessary. In this way the yields amount to 95% to 100% of theory.

By using dimethyl formamide instead of dimethyl sulphoxide and using the ethyl bromide and porassium hydroxide solution respectively in 100% excess, a yield of 80% to 90% of theory of 1-ethyl-2-methyl-indole is obtained after a reaction time of 12 hours at 50° C and otherwise carrying out the process as described above.

The following compounds are obtained in analogous manner from 2-methyl-indole and the alkylating agents listed in Table I.

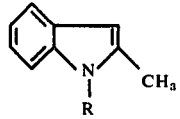

Table I

| Alkylating agent | R | m.p. ° C | b.p. ° C | $nD^{20}$ |
| --- | --- | --- | --- | --- |
| $CH_2=CH-CN$ | $-CH_2-CH_2-CN$ | 795 – 81° | — | — |
| $CH_2=CH-COOH$ | $-CH_2-CH_2-COOH$ | 112 – 113° | — | — |
| $Cl-C_3H_7$ | $-C_3H_7$ | — | b.p. 14    155° | 1,5720 |
| $Br-C_4H_9$ | $-C_4H_9$ | — | b.p. 14    163–165° | 1,5630 |
| $Br-C_5H_{11}$ | $-C_5H_{11}$ | — | b.p. 0.015    101–102° | 1,5540 |

Table I-continued

| Alkylating agent | R | m.p. °C | b.p. °C | | nD²⁰ |
|---|---|---|---|---|---|
| Br—C₆H₁₃ | —C₆H₁₃ | — | b.p. 0.7 | 128–133° | 1,5470 |
| Br—C₇H₁₅ | —C₇H₁₅ | — | b.p. 0.015 | 115–116° | 1,5370 |
| Br—C₈H₁₇ | —C₈H₁₇ | — | b.p. 0.015 | 120–121° | 1,5300 |
| Br—C₉H₁₉ | —C₉H₁₉ | — | b.p. 0.02 | 136–137° | 1,5290 |
| Br—C₁₀H₂₁ | —C₁₀H₂₁ | — | b.p. 0.02 | 137–138° | 1,5200 |
| Br—C₁₂H₂₅ | —C₁₂H₂₅ | — | b.p. 0.02 | 163° | 1,5180 |
| Br—C₁₈H₃₇ | —C₁₈H₃₇ | 38 – 40° | b.p. 0.01 | 219–222° | — |
| Cl—CH₂—CH=CH₂ | —CH₂—CH=CH₂ | — | b.p. 0.015 | 89° | 1,5886 |
| Br—(CH₂)₁₀—COOH | —(CH₂)₁₀—COOH | — | b.p. 0.02 | 184–186° | 1,5136 |
| CH₂—CH—CH₂—CH₃ \\ / O | —CH₂—CH—CH₂—CH₃ \| OH | — | b.p. 0.02 | 122–126° | 1,5775 |
| CH₂—CH—CH₃ \\ / O | —CH₂—CH—CH₃ \| OH | — | b.p. 0.02 | 122–123° | 1,5893 |
| CH₂=CH—COOC₂H₅ | —C₂H₄—COO—C₂H₅ | — | b.p. 0.02 | 134° | 1,5589 |

By using an equivalent amount of 2-phenyl-indole instead of 2-methyl-indole and otherwise carrying out the process in analogous manner, the following compounds are obtained:

Table II

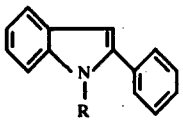

| Alkylating agent | R | m.p. °C | b.p. °C | | nD²⁰ |
|---|---|---|---|---|---|
| C₂H₅—Br | —C₂H₅ | 82 – 83° | — | | — |
| C₃H₇—Br | —C₃H₇ | — | b.p. 0.01 | 125–127° | 1,6333 |
| C₄H₉—Br | —C₄H₉ | — | b.p. 0.01 | 128–129° | 1,6199 |
| C₅H₁₁—Br | —C₅H₁₁ | — | b.p. 0.01 | 140–141° | 1,6127 |
| C₈H₁₇—Br | —C₈H₁₇ | — | b.p. 0.01 | 175° | 1,5858 |
| C₁₂H₂₅—Br | —C₁₂H₂₅ | — | b.p. 0.01 | 207–210° | 1,5700 |
| C₁₈H₃₇—Br | —C₁₈H₃₇ | 47 – 49° | — | | — |
| C₆H₁₃—Br | —C₆H₁₃ | — | b.p. 0.02 | 153–156° | 1,6028 |
| C₇H₁₅—Br | —C₇H₁₅ | — | b.p. 0.01 | 157–158° | 1,5937 |
| C₉H₁₉—Br | —C₉H₁₉ | — | b.p. 0.01 | 173–180° | 1,5839 |
| C₁₀H₂₁—Br | —C₁₀H₂₁ | — | b.p. 0.02 | 178–185° | 1,5792 |
| CH₂—CH—CH₂—CH₃ \\ / O | —CH₂—CH—CH₂—CH₃ \| OH | — | b.p. 0.02 | 164–166° | 1,6340 |
| CH₂—CH—CH₃ \\ / O | —CH₂—CH—CH₃ \| OH | — | b.p. 0.03 | 161–162° | 1,6508 |

The following compounds are obtained in analogous manner from indole:

Table III

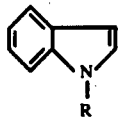

| Alkylating agent | R | b.p. °C | | nD²⁰ |
|---|---|---|---|---|
| C₂H₅—Br | —C₂H₅ | b.p. 11 | 117° | 1,5903 |
| C₄H₉—Br | —C₄H₉ | b.p. 0.02 | 86 – 88° | 1,5659 |
| C₆H₁₃—Br | —C₆H₁₃ | b.p. 0.02 | 105 – 108° | 1,5493 |
| C₈H₁₇—Br | —C₈H₁₇ | b.p. 0.01 | 115° | 1,5376 |

By treating in analogous manner 5-methoxy-indole with n-butyl bromide, 1-n-butyl-5-methoxy-indole is obtained (b.p.:103°-104° C, nD²⁰ : 1.5674).

EXAMPLE 2

131.2 Parts of 2-methylindole, 49 parts of sodium hydroxide flake (containing 95% of NaOH and 5% of water) and 300 parts by volume of dimethyl sulphoxide are heated to 45° C and stirred at 45° C for 15 minutes. 77 Parts of ethyl chloride are passed into the reaction mixture by means of a delivery tube underneath the surface, over 2 hours at 45°–50° C. The mixture is then stirred at 45°–50° C for 3 hours. The completion of reaction is detected by thin-layer chromatography. The precipitated sodium chloride is separated by filtration and washed with 50 parts dimethyl sulphoxide which is then combined with the filtrate. 200 Parts by volume of water at 60° C are added to the combined filtrates, stirred, and then allowed to separate into two layers. The upper oily layer is removed and washed twice with 10% brine. The crude oily product thus obtained is of suitable industrial quality containing 96% 1-ethyl-2-methylindole and 4% 1,3-diethyl-2-methylindole. Yield is 84.3% of theory.

We claim:
1. A process for the manufacture of N-substituted indoles, which comprises treating indole or mono- or disubstituted indole substituted with alkyl or alkoxy with 1 to 4 carbon atoms, halogen, phenyl, tolyl, chlorophenyl or methoxyphenyl with non-aqueous alkali hydroxide in dimethyl sulfoxide, dimethyl formamide or dimethyl acetamide, and subsequently reacting with an alkylating agent which is a member selected from the group consisting of an alkyl halide with up to 18 carbon atoms, an alkenyl halide with up to 18 carbon atoms, a benzyl halide, an alkene of the formula

$$CH_2 = CH - Y$$

in which Y is cyano, carboxy or carbalkoxy with 1 to 4 carbon atoms in the alkoxy radical, and an epoxide of the formula

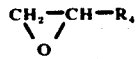

in which $R_4$ is alkyl with 1 to 4 carbon atoms or halogenalkyl with 1 to 4 carbon atoms, whereby 100% to 150% of the stoichiometrically requisite amount of the alkylating agent is used and the process is carried out at temperatures of up to 50° C and in the substantial absence of water.

2. A process according to claim 1, wherein starting materials are indoles which carry as substituents alkyl or alkoxy of 1 to 4 carbon atoms, phenyl, toluyl, chlorophenyl or methoxy phenyl.

3. A process according to claim 1, wherein staring material is 2-methyl-indole.

4. A process according to claim 1, wherein the process is carried out in dimethyl sulphoxide.

5. A process according to claim 1, wherein the alkylating agent is ethyl bromide or ethyl chloride.

6. A process according to claim 1, wherein the alkylating agent is n-octyl bromide.